US00PP11693P

United States Patent [19]

Vanderhaegen

[11] Patent Number: Plant 11,693

[45] Date of Patent: Dec. 12, 2000

[54] AZALEA PLANT NAMED 'CHRISTINE MATTON'

[75] Inventor: Johan Vanderhaegen, Kruishoutem, Belgium

[73] Assignee: Hortibreed N.V., Lochristi, Belgium

[21] Appl. No.: 09/259,357

[22] Filed: Mar. 1, 1999

[51] Int. Cl.[7] ..... A01H 5/00

[52] U.S. Cl. ..... Plt./239

[58] Field of Search ..... Plt./239, 238, 240

*Primary Examiner*—Bruce R. Campell
*Assistant Examiner*—Kent L. Bell
*Attorney, Agent, or Firm*—C. A. Whealy

[57] ABSTRACT

A new and distinct cultivar of Azalea plant named 'Christine Matton', characterized by its vigorous and dense plants that are very freely branching; uniform, upright and outwardly spreading plant habit; very dark green shiny foliage; freely flowering, showy double salmon-pink flowers; and long flowering period.

1 Drawing Sheet

BACKGROUND OF THE INVENTION

The present invention relates to a new and distinct cultivar of Azalea, botanically known as *Rhododendron hybrida*, an evergreen greenhouse-forcing type, and hereinafter referred to by the name 'Christine Matton'.

The new Azalea is a product of a planned breeding program conducted by the Inventor in Kruishoutem, Belgium. The objective of the breeding program is to create new potted Azelea varieties that root well and are easy to grow and have uniform plant habit, dark green foliage, numerous flowers with unique flower color, and stay in flower for a long period of time.

The new Azalea originated from a cross made by the Inventor in 1990 in Kruishoutem, Belgium, of the proprietary seedling selection of *Rhododendron hybrida* identified as 0020 as the female, or seed, parent with an unidentified seedling selection of *Rhododendron hybrida* as the male, or pollen, parent.

The new Azalea was discovered and selected by the Inventor as a flowering plant within the progeny of the stated cross in a controlled environment in Kruishoutem, Belgium. The selection of this plant was based on its very dark green shiny foliage, unique flower color and freely branching growth habit.

Asexual reproduction of the new Azalea by terminal cuttings taken in a controlled environment in Kruishoutem, Belgium, has shown that the unique features of this new Azalea are stable and reproduced true to type in successive generations.

BRIEF SUMMARY OF THE INVENTION

The new Azalea has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Christine Matton'. These characteristics in combination distinguish 'Christine Matton' as a new and distinct cultivar:

1. Vigorous and dense plants that are very freely branching.
2. Uniform, upright and outwardly spreading plant habit.
3. Very dark green shiny foliage.
4. Freely flowering, showy double salmon-pink flowers.

5. Long flowering period; plants stay in flower for more than three weeks.

Plants of the new Azalea can be compared to plants of the commercial cultivar 'Marie Claude Truffaut' (not patented). However, in side-by-side comparisons conducted in Kruishoutem, Belgium, plants of the new Azalea are more vigorous, are more freely branching, have darker green and shinier leaves, and flower earlier than plants of the cultivar 'Marie Claude Truffaut'.

Plants of the new Azalea can also be compared to plants of the commercial cultivar 'Mevrouw Andre Heugens' (not patented). However, in side-by-side comparisons conducted in Kruishoutem, Belgium, plants of the new Azalea are more freely branching and have darker green and shinier leaves than plants of the cultivar 'Mevrouw Andre Heugens'.

BRIEF DESCRIPTION OF THE PHOTOGRAPHS

The accompanying colored photographs illustrate the overall appearance of the new Azalea, showing the colors as true as it is reasonably possible to obtain in colored reproductions of this type.

The photograph at the top of the sheet comprises a top perspective view of a typical plant of 'Christine Matton'.

The photograph at the bottom of the sheet is a close-up view of typical flowers of 'Christine Matton'. Flower and foliage colors in the photographs may appear different from the actual colors due to light reflectance.

DETAILED BOTANICAL DESCRIPTION

The aforementioned and following observations, measurements, values, and comparisons describe plants grown in Kruishoutem, Belgium, in 12-cm containers under conditions which approximate commercial Azalea production conditions. In the following description, color references are made to The Royal Horticultural Society Colour Chart except where general terms of ordinary dictionary significance are used.

Botanical classification:

*Botanical.*—*Rododendron hybrida* 'Christine Matton'.

*Commercial.*—Evergreen greenhouse-forcing type Azalea.

Parentage:

*Male or pollen parent.*—Unidentified proprietary seedling selection of *Rhododendron hybrida*.

*Female or seed parent.*—Proprietary seedling selection of *Rhododendron hybrida* identified as 0020.

Propagation:

*Type.*—By terminal cuttings.

*Time to develop roots.*—Summer: About 50 days at temperatures of 22°C. Winter: About 60 days at temperatures of 22°C.

*Rooting habit.*—Vigorous and finely-branched.

Plant description:

*Plant form and growth habit.*—Perennial, evergreen, upright and outwardly spreading, rounded, uniform plant habit. Vigorous. Numerous flowers per plant. Appropriate for 12 to 16-cm containers.

*Branching habit.*—Freely branching; usually about ten lateral branches develop after removal of terminal apex.

*Plant height, soil level to top of flowers.*—About 20 cm.

*Plant diameter, area of spread.*—About 30 cm.

*Growth rate.*—Moderate; about 8 to 15 cm of growth per year.

*Lateral branch description.*—Length: About 8 to 15 cm. Diameter: About 3 mm. Internode length: About 1 to 2 cm. Color/texture: Mature, brown woody; young, green with sparse reddish-brown hairs.

Foliage description:

*Arrangement.*—Alternate to whorled at end of branches.

*Quantity of leaves per lateral branch.*—About 15 to 25.

*Length.*—About 2 to 5.5 cm.

*Width.*—About 1.5 to 3 cm.

*Shape.*—Elliptic.

*Apex.*—Obtuse.

*Base.*—Acute.

*Margin.*—Entire.

*Texture.*—Leathery, glabrous.

*Color.*—Young foliage, upper surface: Dark green, 137A. Young foliage, lower surface: 138A to 138B. Mature foliage, upper surface: Very dark green, close to 139A. Mature foliage, lower surface: 147A to 147B. Venation, upper surface: 144A to 144B. Venation, lower surface: 143C.

*Petiole.*—Length: About 5 mm or less. Color: Close to 144A to 144B.

Flower description:

*Natural flowering season.*—Spring after sufficient cool period.

*Flower arrangement.*—Flowers arranged singly at terminals. Flowers typically have five petals surrounding at least five stamenoidal petaloids. The quantity of petaloids may be dependent on environmental conditions. Flowers face upward and outward. Very freely flowering.

*Flower appearance.*—Showy star-shaped double flowers. Salmon-pink in color. Flowers persistent.

*Postproduction longevity.*—Plants maintain good flower substance for more than three weeks.

*Flower bud.*—Length: About 2 to 4 cm. Diameter: About 1 to 1.5 cm. Shape: Narrowly ovoid. Color: 137A to 137B.

*Petals and petaloids.*—Arrangement: Double. Shape: Spatulate with rounded apex. Margin: Entire with slightly undulating edge which gives a ruffled appearance. Length: Petals: About 5 cm. Petaloids: About 4 to 5 cm. Width: Petals: About 4 cm. Petaloids: About 2 to 3 cm. Texture: Smooth, satiny. Color: When opening, upper and lower surfaces: Towards base, 48D; towards margin, 48D to 50D. Fully opened, upper and lower surfaces: Towards base, 48D; towards margin, 48D to 50D. With subsequent development, petal and petaloid color more towards 48C.

*Sepals.*—Arrangement: Five sepals fused into a star-shaped calyx. Texture: Very pubescent. Shape: Ovate. Margin: Entire. Color: Upper surface, 144C; lower surface, 144C to 144D.

*Peduncles.*—Length: About 1 cm. Diameter: About 3 to 4 mm. Angle: Erect. Strength: Flexible, strong. Color: 144D.

*Reproductive organs.*—Androecium: No stamens observed. Gynoecium: Pistil quantity: One. Pistil length: About 1.5 to 2.5 cm. Stigma shape: Oval. Stigma color: 48D. Style length: About 1.2 to 2.2 cm. Style color: Base, 143C; towards apex, 50D to 50C. Ovary: Whiskered; 141B in color.

Disease resistance: Resistance to known pathogens of Azalea has not been observed on plants grown under commercial greenhouse conditions.

Seed production: Seed production has not been observed.

It is claimed:

1. A new and distinct Azalea plant named 'Christine Matton', as illustrated and described.

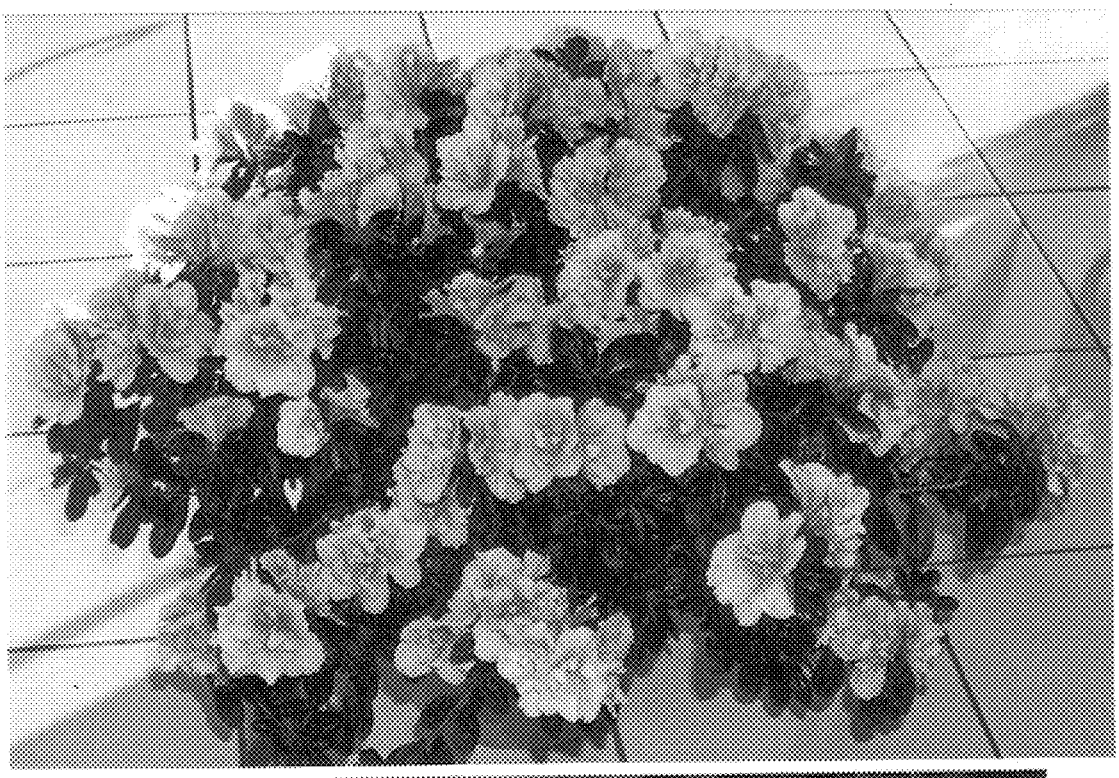
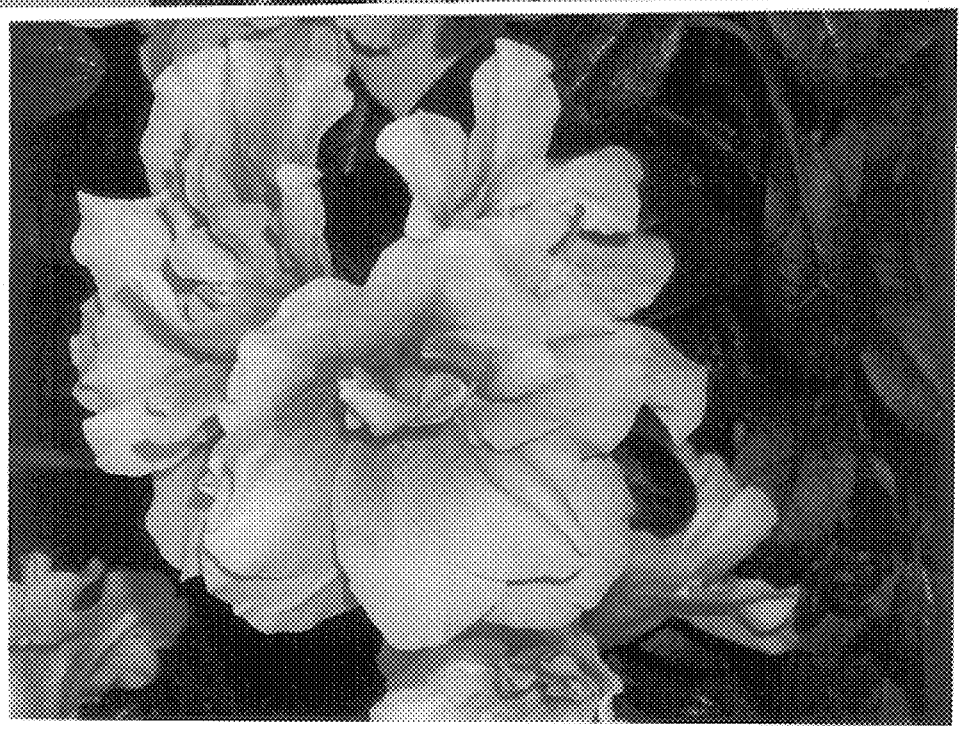

* * * * *